United States Patent [19]

Farkas

[11] Patent Number: 5,267,988
[45] Date of Patent: Dec. 7, 1993

[54] NON-INVASIVE FEMALE URINE COLLECTION DEVICE

[76] Inventor: Barry L. Farkas, 5417 Plainfield St., Pittsburgh, Pa. 15217

[21] Appl. No.: 981,786

[22] Filed: Nov. 25, 1992

[51] Int. Cl.⁵ .................. A61F 5/44; A61B 5/00; B65D 81/00; A47K 11/00
[52] U.S. Cl. ..................... 604/329; 128/761; 4/144.3
[58] Field of Search ............. 128/760, 761; 604/329-331; 4/144.1-144.3

[56] References Cited

U.S. PATENT DOCUMENTS

| | | | |
|---|---|---|---|
| 3,194,238 | 7/1965 | Breece, Jr. | 604/329 |
| 4,484,917 | 11/1984 | Blackmon | 604/327 |
| 4,496,355 | 1/1985 | Hall et al. | 604/327 |
| 4,568,339 | 2/1986 | Steer | 604/329 |
| 4,631,061 | 12/1986 | Martin | 604/318 |
| 4,692,160 | 9/1987 | Nussbaumer | 604/331 |
| 4,713,065 | 12/1987 | Koot | 604/329 |
| 4,747,166 | 5/1988 | Kuntz | 4/144.1 |
| 4,813,943 | 3/1989 | Smith | 604/329 |
| 4,822,347 | 4/1989 | MacDougall | 604/329 |
| 4,846,817 | 7/1989 | Mohr et al. | 604/329 |
| 4,936,838 | 6/1990 | Cross et al. | 604/329 |
| 5,053,027 | 10/1991 | Manfredi | 604/329 X |

FOREIGN PATENT DOCUMENTS

| | | | |
|---|---|---|---|
| 2129686 | 5/1984 | United Kingdom | 604/329 |
| 8904156 | 5/1989 | World Int. Prop. O. | 604/329 |

OTHER PUBLICATIONS

Clinical Evaluation Of An External Urine Collection Device For Nonambulatory Incontinent Women, Johnson, David E., et al., Journal of Urology, vol. 141, Mar., pp. 535-537, 1989.
An External Urine Collection Device for Incontinent Women—Evaluation of Long-Term Use, Johnson, David E., Journal of American Geriatrics Society, Sep. 1990, vol. 38, No. 9, pp. 1016-1022.

Primary Examiner—Randall L. Green
Assistant Examiner—Elizabeth M. Burke
Attorney, Agent, or Firm—Webb, Burden, Ziesenheim & Webb

[57] ABSTRACT

A non-invasive female urine collection device includes an elongated pad adapted to be positioned comfortably between the legs of a female patient and against the patient's perineal area. The pad includes a flat, planar base having an outlet extending between an inner surface and an outer surface thereof. A flexible membrane is positioned above the inner surface of the base and has an outer circumferential edge attached to the base, preferably along an outer edge of the base. The flexible membrane has an inner circumferential edge which defines an open area therein, with the inner circumferential edge of the flexible membrane surrounding the outlet, preferably immediately adjacent the outlet, and attached to the inner surface of the base. The inner circumferential edge and outer circumferential edge of the flexible membrane are spaced apart from each other that a chamber is formed between the flexible membrane and the base. The chamber can be inflated and form a comfortable cushion when the flexible membrane is positioned against a patient's perineal area. A portion of the flexible membrane adjacent the inner circumferential edge forms a flow channel which extends from an opening at an outer surface of the membrane to the outlet. The opening of the flow channel at the flexible membrane outer surface is adapted configured to surround the patient's urethra.

24 Claims, 4 Drawing Sheets

NON-INVASIVE FEMALE URINE COLLECTION DEVICE

BACKGROUND OF THE INVENTION

1. Field Of The Invention

This invention relates to urinary devices and, more particularly, to an external urinary collection device for use by females.

2. Background Art

The number of women who are incontinent of urine is enormous. There are several physiologic bases for such urinary incontinence, with many principal and overlapping causes. The bladder may be spastic and void small amounts of urine on a frequent basis. Loss of pelvic muscle tone may result in stress incontinence where the bladder is fully or partially emptied during any activity that results in increased intra-abdominal pressure (e.g., coughing, sneezing, laughing, standing). More importantly, a patient may have lost cognitive functioning or physical control from medication, surgical complications, mental disorders, or the like and may have no effective bladder control. Patients confined to a bed can also be considered as incontinent and in need of assistance with urine control. Current methods of dealing with this major problem of urinary incontinence are inadequate.

Because no prior external urine collection device has proven satisfactory, only two means are currently available and regularly used for addressing the problem of female incontinence. Women are either diapered, with the attendant indignity, and odor and risk of skin breakdown for practical lack of frequent changing, or they are chronically catheterized with an indwelling bladder tube. While bladder catheterization usually maintains dryness and is convenient for patient caretakers, it also virtually guarantees infection. Even when introduced aseptically, the bladder's defenses against infection are breached. Bacteria on the external genito-urinary area use the catheter surface to ascend into the bladder, where they rapidly multiply in an ideal environment for growth. Urinary tract infections of the bladder and kidneys, with spreading thence into the blood stream, are a common occurrence for internally catheterized patients and are a particular problem in patients catheterized for periods longer than forty-eight hours.

There has been a recognized need for quite some time for a practical, effective and safe external catheter or urine collection device for females. U.S. Pat. No. 4,822,347 discloses a urine collection device that is adhesively attached to the skin of the wearer in the region immediately surrounding the urethral orifice. However, this device is relatively uncomfortable for a patient and cannot remain in place for extended periods of time without causing skin discomfort or trauma. A number of other external female catheters have been suggested in the prior art as shown in U.S. Pat. Nos. 3,194,238; 4,484,917; 4,496,355; 4,568,339; 4,631,061; 4,713,065; 4,747,166; 4,813,943; 4,846,817; 4,936,838; and U.S. Pat. No. 5,053,027. These devices have a number of problems which render all of them ineffective for use on a practical basis. Most of these devices are molded into particular configurations and are not readily adapted for use by a wide range of females having varying physical characteristics, sizes and the like. In addition, several of these devices must be placed within the labial lips of a patient, causing discomfort and embarrassment. Basically, the prior external female catheters are not practical for extended use on a wide range of female patients.

It is, therefore, an object of the present invention to provide an effective and comfortable means of urine collection for women who are either incontinent of bladder or who are incapacitated and cannot use a toilet. It is a further object to provide such a urine collection device which can result in a custom fit on an individualized basis for various female patients. It is yet a further object to provide a urine collection device which has maximum efficacy and enhanced safety.

SUMMARY OF THE INVENTION

Accordingly, I have developed a non-invasive female urine collection device which includes an elongated pad adapted to be positioned comfortably between the legs of a female patient and in contact with at least a portion of the patient's perineal area. The pad includes a flat, planar base having an outlet extending between an inner surface and an outer surface thereof. A flexible membrane is positioned above the inner surface of the base and has an outer circumferential edge attached to the base, preferably along an outer edge of the base. The flexible membrane has an inner circumferential edge which defines an open area therein, with the inner circumferential edge of the flexible membrane surrounding the outlet, preferably immediately adjacent the outlet, and attached to the inner surface of the base. The inner circumferential edge and outer circumferential edge of the flexible membrane are spaced apart from each other such that a chamber is formed between the flexible membrane and the base. The chamber is configured to be inflated and form a comfortable cushion when the flexible membrane is positioned against a patient's perineal area. A portion of the flexible membrane adjacent the inner circumferential edge forms a flow channel which extends from an opening at an outer surface of the membrane to the outlet. The opening of the flow channel at the flexible membrane outer surface is configured to surround the patient's urethra. The device further can include a means for inflating the chamber, such as an air nipple in fluid communication with the chamber, or the device can be manufactured with the chamber preinflated.

The device can further include a support means for securing the pad to a female patient with the flexible membrane contacting the patient's perineal area. The support means can include a plurality of strap holding tabs attached to the base, a strap attached at a lower end to each of the tabs, a support belt configured to encircle the patient's waist, and attachment means for attaching an upper end of each of the straps to the support belt. The attachment means can include adjustment means for adjusting the tension on the straps and for adjusting the location of the upper ends of the straps on the support belt.

The invention can also include drainage means connected to the outlet for draining fluids flowing into the flow channel. An outlet nipple can be positioned on an outer surface of the base and in fluid communication with the outlet. A drain conduit can be connected at a first end to the outlet nipple. A collection means can be connected to a second end of the drain conduit and draw fluids through the drain conduit to a collection holding vessel.

It is preferred that the base and flexible membrane be formed of a clear plastic material. In addition, it is preferred that the outer surface of the flexible membrane defining the flow channel and immediately surrounding the opening be coated with a layer of a hydrophobic material.

DESCRIPTION OF THE PREFERRED EMBODIMENT

Figure 1:
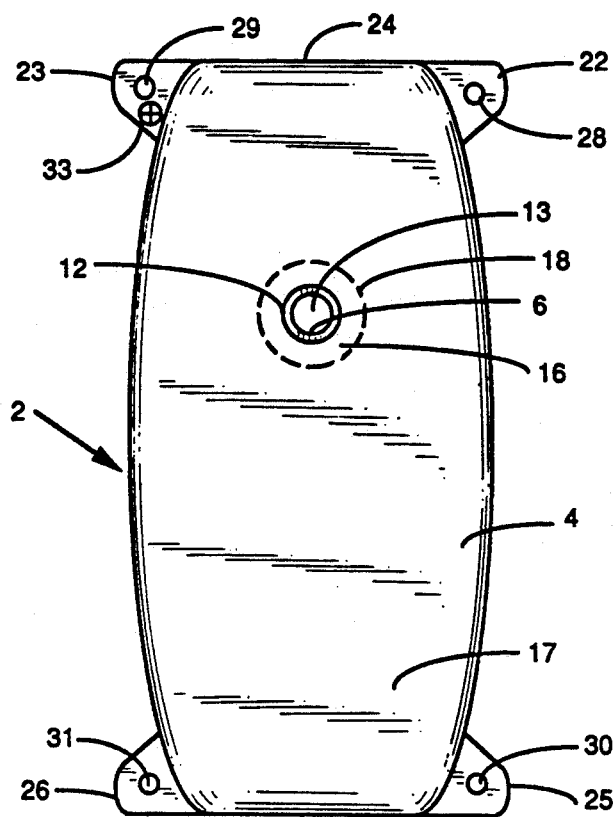
FIG. 1 is an outer plan view of a non-invasive female urine collection device in accordance with the present invention.
Figure 2:
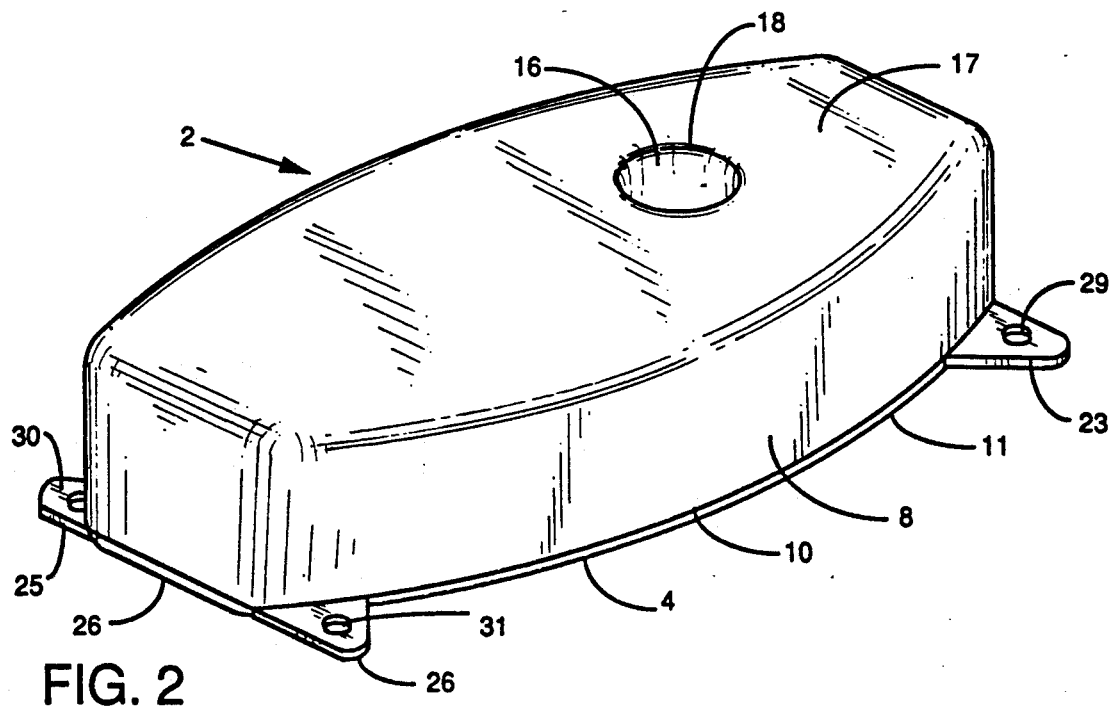
FIG. 2 is an inner, perspective view of the urine collection device shown in FIG. 1.
Figure 3:
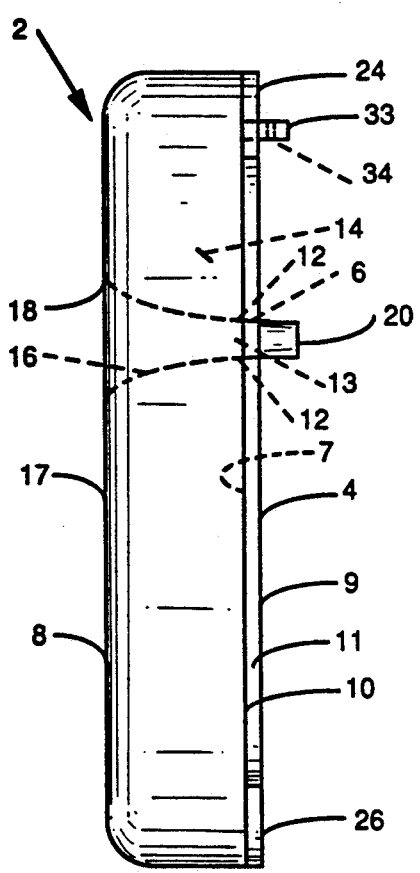
FIG. 3 is a side view of the urine collection device shown in FIG. 1.

A non-invasive female urine collection device in accordance with the present invention is shown in FIGS. 1-3. The urine collection device is formed of an elongated pad 2 which is adapted to be positioned between the legs of a female patient and in contact with at least a portion, preferably a large portion, of the patient's perineal area. The pad 2 includes an elongated, flat, planar base 4 having an outlet 6 extending between an inner surface 7 and an outer surface 9 of the base 4. A flexible membrane 8 is positioned above the inner surface 7 of the base 4 and has its outer circumferential edge 10 attached to the base 4, preferably along the outer edge 11 of the base 4 as shown. The flexible membrane 8 has an inner circumferential edge 12 which defines an open area 13 in an interior area thereof. The inner circumferential edge 12 surrounds the outlet 6, preferably immediately surrounding the outlet 6 as shown, and is attached to the inner surface 7 of the base 4. The inner circumferential edge 12 and outer circumferential edge 10 of the membrane 8 are spaced apart from each other such that a chamber 14 is formed between the membrane 8 and the base 4. As will be explained hereinafter in more detail, the chamber 14 can be preinflated with air when the pad 2 is initially manufactured or, as is preferred, can be inflated after the pad 2 has been positioned against a particular female patient.

A portion of the flexible membrane 8 adjacent its inner circumferential edge 12 defines a flow channel 16 which extends from an opening 18 at an outer surface 17 of the membrane 8 and to the outlet 6. The outer surface 9 of the base 4 carries an outlet nipple 20 surrounding and in fluid communication with the outlet 6 in the base 4. It is preferred that the opening 18 have a diameter larger than that of the outlet 6 and that the flow channel 16 taper inwardly and have a gradually reducing diameter as the flow channel 16 extends from the opening 18 to the outlet nipple 20.

Strap tabs 22, 23, 25 and 26 are provided along the outer edge 11 of the base 4 and are attached thereto at several locations. As shown in FIG. 1, upper strap tabs 22 and 23 are positioned at an upper end 24 of the base 4 and on opposite sides thereof. Similarly, lower strap tabs 25 and 26 are positioned at a lower end 27 of the base 4 and on opposite sides thereof. Strap tabs 22, 23, 25 and 26 each have a hole 28, 29, 30 and 31, respectively, therethrough for accommodating a support strap as will be discussed hereinafter in more detail.

Figure 4:
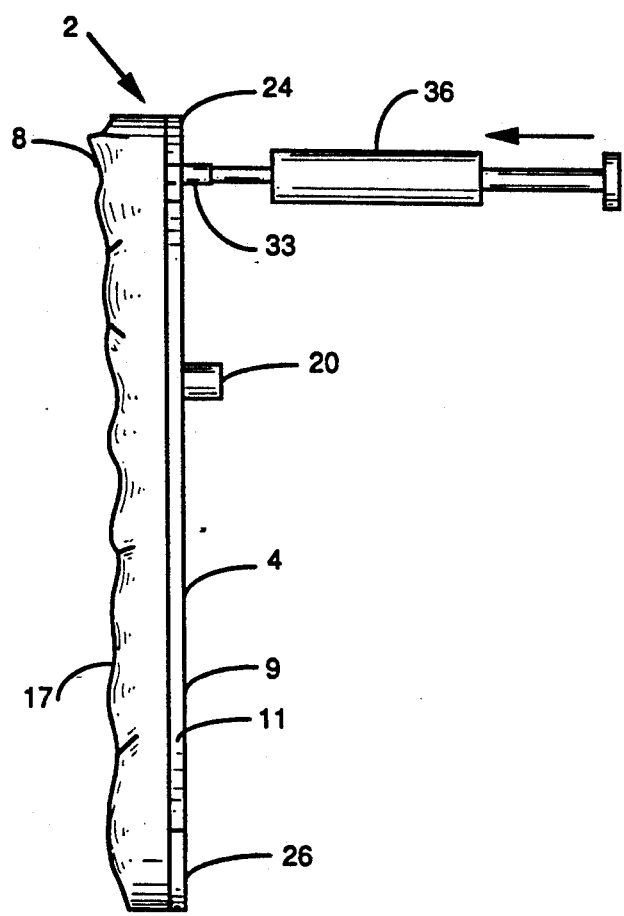
FIG. 4 is a side view, similar to FIG. 3, of the urine collection device of FIG. 1 being inflated.

An air inlet nipple 33 is shown attached to strap tab 23 and in fluid communication with the chamber 14 between the membrane 8 and the base 4. As shown in FIG. 3, the air inlet nipple 33 includes a normally closed valve 34 therein to keep air from flowing out of the chamber 14. The chamber 14 is filled with a quantity of air such that the membrane 8 forms a low pressure, high volume air inflated cushion. The chamber 14 can be preinflated at a manufacturing facility, and be shipped as shown in FIG. 3. Alternately, and preferably, the chamber 14 can be inflated after the urine collection device has been positioned against the female patient. As shown in FIG. 4, the device can be inflated by inserting an air syringe 36 into the air inlet nipple 33 and inserting air into the chamber 14 until the membrane 8 is inflated to a desired level.

Figure 5:
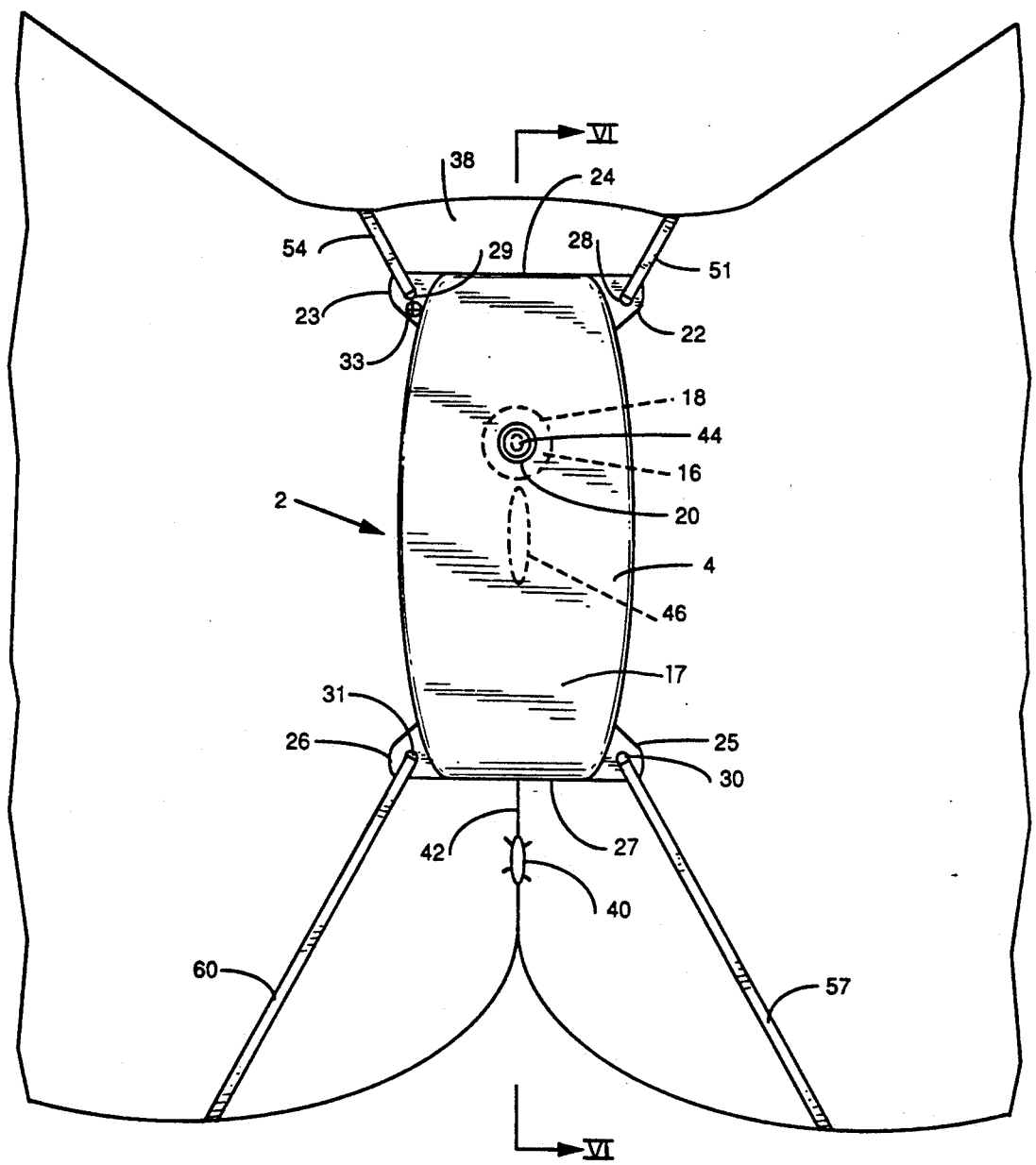
FIG. 5 is a ventral view of a patient wearing the urine collection device of FIG. 1.
Figure 6:
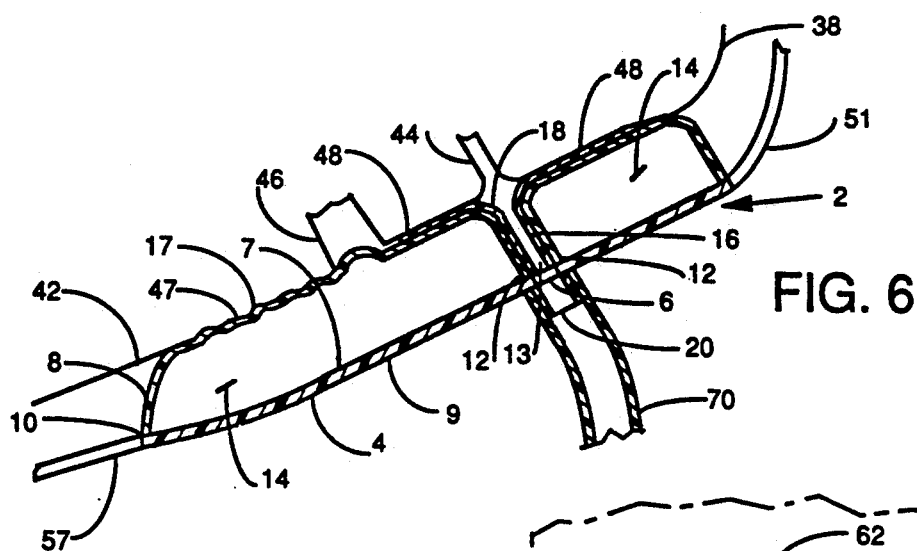
FIG. 6 is a section taken along lines VI—VI in FIG. 5.

When inflated, the pad 2 of the present invention resembles a perineal pad. It is preferred that the pad 2 be configured to comfortably fit between a female patient's legs and cover the perineal area beyond the lateral margins of the labia, anteriorly to the mons pubis 38 and posteriorly to the perineal raphe 42, as depicted in FIGS. 5 and 6 which show the urine collection device of the present invention attached to a female patient. The pad 2 is positioned with the upper end 24 of the base 4 below the mons pubis 38 and the lower end 27 of the base 4 above the patient's anus 40 and terminating at about the perineal raphe 42. The membrane 8 of the pad 2 is positioned against the perineal area of the patient and the base 4 is positioned away from the patient. The opening 18 of the flow channel 16 is positioned surrounding the patient's urethra 44, but the opening 18 is preferably configured such that it does not extend to the patient's vagina 46. Rather, the patient's vagina 46 and labia 47 would be completely covered by the outer surface 17 of the membrane 8. The air inflated membrane 8 conforms to a patient's perineal surface to form a tight fit therewith.

As shown in FIG. 6, the area of the outer surface 17 of the membrane 8 surrounding the opening 18, along with the surface of the flow channel 16 therein, is preferably coated with a layer of a hydrophobic or urine repelling material 48, such as Teflon ® or other commercially available materials. The air cushion membrane 8 is designed to encircle the periurethral zone of the patient without obstructing the free flow of urine into the flow channel 16, but also prevent urine from leaking into a patient's vagina 46 or other perineal areas. The hydrophobic material 48 both helps to direct the flow of urine into the flow channel 16, but also keeps the moisture in the area near the flow channel 16 away from the patient's skin. A hydrophobic or urine repelling material, such as Desitin ® or the like, can be topically applied directly to the patient's periurethral area. This topical coating both protects the patient's skin and helps direct the flow of urine into the flow channel 16.

Figure 7:
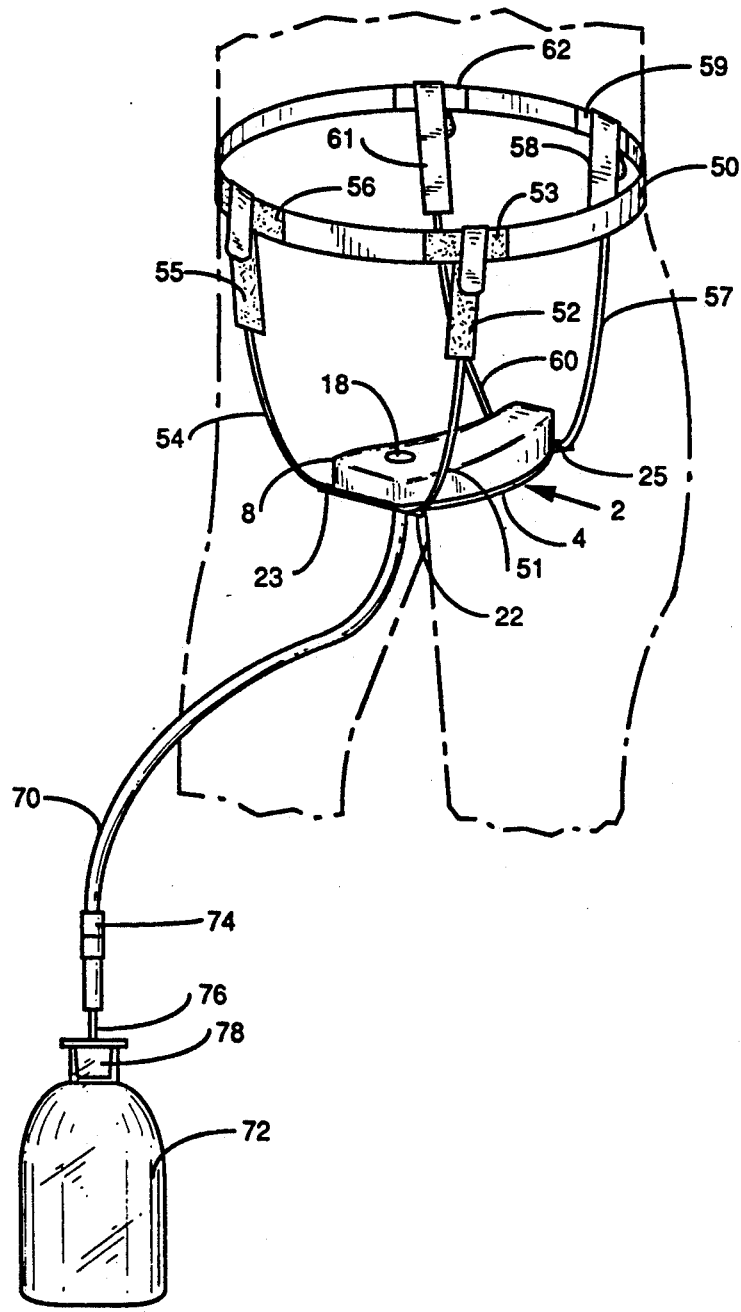
FIG. 7 is a perspective view of the urine collection device shown in FIG. 1 attached to a female patient and to a urine collection container.

An arrangement by which the pad 2 of the present invention can be attached to a patient is shown in FIG. 7, with additional reference to FIGS. 5 and 6. A waist encircling support belt 50 preferably includes a separate attachment area, such as a section of Velcro ®, on its outer surface for each strap tab on the base 4. A thin strap is attached at a lower end to each strap tab by way of the associated strap tab hole. An upper end of each strap has a strap connector, preferably a wider area covered with Velcro ® or other attachment means compatible with the attachment areas on the belt 50. The upper end of each strap is looped behind the waist belt 50, with the smooth portion of the strap connector in contact with the patient. The strap connector is then looped around the belt 50 and affixed to the respective attachment area on the outer surface of the belt 50. In particular, strap 51 is attached to strap tab 22 and has strap connector 52 affixed to attachment area 53 on the belt 50. Similarly, strap 54 is attached to strap tab 23 and has strap connector 55 affixed to attachment area 56 on the belt 50. Likewise, strap 57 is attached to strap tab 25 and has strap connector 58 attached to attachment area 59 on the belt 50. Finally, strap 60 is attached to strap tab 26 and has strap connector 61 attached to attachment area 62 on the belt 50. The tension on each strap can be adjusted by adjusting the size of the loop of the strap connector surrounding the belt 50. The location of the strap connector on the attachment area on the belt 50 can be adjusted laterally to provide a comfortable fit. It is believed that four straps are ideal, although fewer or greater numbers of straps can be used if desired.

As shown in FIGS. 6 and 7, the outlet nipple 20 on the base 4 of the pad 2 is connected to a drain conduit 70. The drain conduit 70 can extend to and pass urine to any of a variety of urine collection vessels. In the embodiment shown in FIG. 7, the drain conduit 70 is connected to a vacuum bottle 72 which positively draws any of the patient's expelled urine through the drain conduit 70 and into the vacuum bottle 72. The end of the drain conduit 70 opposite the outlet nipple 20 is attached to a connector 74 which, in turn, is attached to a needle 76. The needle 76 pierces a bottle stopper 78 in the vacuum bottle 72 and maintains the vacuum therein.

The membrane 8 is preferably formed of a biologically inert gas and liquid impermeable, flexible plastic material, such as silicone rubber. The base 4 is significantly stiffer than the membrane 8, but is also formed preferably of biologically inert and liquid and gas impermeable material. While the base 4 may have some flexibility to it, it should provide an inflexible support to the inflated membrane 8 that it carries. It is also preferred that the membrane 8 and base 4 be formed of a clear material.

The air cushion formed by the inflated membrane 8 will tend to conform to a patient's anatomy and form an effective seal around the patient's urethical opening. In addition, by inflating the membrane 8 after the pad 2 has been positioned against a female's perineal area, a proper amount of air can be inserted into the chamber 14 to provide a precise and customized fit. The use of clear plastic for the membrane 8 and base 4 will enable a physician or other caretaker to properly position the pad 2 with the opening 18 of the flow channel 16 just surrounding the urethra 44 while keeping the patient's vagina 46 covered by the outer surface 17 of the membrane 8. The inflated membrane 8 provides a soft, pliable contour-seeking seal against the patient's perineum and should be large enough to provide a comfortable, cushioning fit and maintain a seal to direct the urine flow into the flow channel 16.

The result of this invention is a comfortable, reliable and dignified means for collecting urine from an incontinent female patient. By providing the pad 2 in only several basic sizes, patients having wide variations of physiology and anatomical features can be accommodated. In addition, by inflating the membrane 8 in situ, a caretaker can ensure that the fit is customized for an individual patient. The use of the cushioning air inflated membrane 8 will result in very little or no trauma or discomfort to the patient when the pad 2 is in use. By providing an external urine collection device, which also confines the urine to the area just around the urethra, the chance of infection is greatly reduced or eliminated.

Having described herein the presently preferred embodiment of the present invention, it is to be understood that the invention may be otherwise embodied within the scope of the appended claims.

I claim:

1. A non-invasive female urine collection device for a female patient having legs, a perineal area and a waist, said device comprising an elongated pad configured to be positioned comfortably between the legs of the female patient and in contact with at least a portion of the patient's perineal area, said pad including a flat, planar base having an outlet extending between an inner surface and an outer surface thereof and a flexible membrane positioned above the inner surface of the base and having an outer circumferential edge attached to said base, said flexible membrane having an inner circumferential edge thereof which defines an open area therein, with said inner circumferential edge of said flexible membrane surrounding said outlet and attached to said inner surface of said base, with said inner circumferential edge and outer circumferential edge of said flexible membrane spaced apart from each other such that a chamber is formed between the flexible membrane and the base, with said chamber configured to be inflated and form a comfortable cushion when said flexible membrane is positioned against the patient's perineal area, with a portion of said flexible membrane adjacent said inner circumferential edge forming a flow channel which extends from an opening at an outer surface of said flexible membrane to said outlet, and with said opening of said flow channel at said flexible membrane outer surface configured to surround a patient's urethra, said device further including inflation means for inflating the chamber.

2. The non-invasive female urine collection device of claim 1 further including support means for securing said elongated pad to a female patient with said flexible membrane contacting the patient's perineal area and with said flow channel opening surrounding the patient's urethra.

3. The non-invasive female urine collection device of claim 2 wherein said support means includes a plurality of strap holding tabs attached to said base, a strap having a lower end and attached at its lower end to each of said tabs, a support belt configured to encircle the patient's waist, and attachment means for attaching an upper end of each of said straps to said support belt.

4. The non-invasive female urine collection device of claim 3 wherein said attachment means includes adjustment means for adjusting tension on said straps and for adjusting a location of the upper ends of said straps on said support belt.

5. The non-invasive female urine collection device of claim 1 wherein said base and said flexible membrane are formed of a clear, plastic material.

6. The non-invasive female urine collection device of claim 1 wherein the outer circumferential edge of said flexible membrane is attached along an outer edge of said base and wherein the inner circumferential edge of said flexible membrane is attached immediately adjacent the outlet in said base.

7. The non-invasive female urine collection device of claim 1 further including drainage means connected to said outlet for draining fluids flowing into said flow channel.

8. The non-invasive female urine collection device of claim 1 further including an outlet nipple on the outer surface of said base and in fluid communication with the outlet therein.

9. The non-invasive female urine collection device of claim 8 further including a drain conduit having a first end and connected at its first end to said outlet nipple.

10. The non-invasive female urine collection device of claim 9 further including collection means connected to a second end of said drain conduit for drawing fluids through said drain conduit and for holding said fluids.

11. The non-invasive female urine collection device of claim 1 wherein the outer surface of the flexible membrane defining the flow channel and immediately surrounding the opening of the flow channel is coated with a layer of a hydrophobic material.

12. The non-invasive female urine collection device of claim 1 wherein said inflation means is an air inlet nipple in fluid communication with said chamber.

13. A non-invasive female urine collection device for a female patient having legs, a perineal area and a waist, said device comprising an elongated pad configured to be positioned comfortably between the legs of the female patient and in contact with at least a portion of the patient's perineal area, said pad including a flat, planar base having an outlet extending between an inner surface and an outer surface thereof and a flexible membrane positioned above the inner surface of the base and having an outer circumferential edge attached to said base, said flexible membrane having an inner circumferential edge thereof which defines an open area therein, with said inner circumferential edge of said flexible membrane surrounding said outlet and attached to said inner surface of said base, with said inner circumferential edge and outer circumferential edge of said flexible membrane spaced apart from each other such that a chamber is formed between the flexible membrane and the base, with said chamber inflated with air and configured to form a comfortable cushion when said flexible membrane is positioned against the patient's perineal area, with a portion of said flexible membrane adjacent said inner circumferential edge forming a flow channel which extends from an opening at an outer surface of said flexible membrane to said outlet, and with said opening of said flow channel at said flexible membrane outer surface configured to surround a patient's urethra.

14. The non-invasive female urine collection device of claim 13 further including support means for securing said elongated pad to a female patient with said flexible membrane contacting the patient's perineal area and with said flow channel opening surrounding the patient's urethra.

15. The non-invasive female urine collection device of claim 14 wherein said support means includes a plurality of strap holding tabs attached to said base, a strap having a lower end and attached at its lower end to each of said tabs, a support belt configured to encircle the patient's waist, and attachment means for attaching an upper end of each of said straps to said support belt.

16. The non-invasive female urine collection device of claim 15 wherein said attachment means includes a adjustment means for adjusting tension on said straps and for adjusting a location of the upper ends of said straps on said support belt.

17. The non-invasive female urine collection device of claim 13 wherein said base and said flexible membrane are formed of a clear plastic material.

18. The non-invasive female urine collection device of claim 13 wherein the outer circumferential edge of said flexible membrane is attached along an outer edge of said base and wherein the inner circumferential edge of said flexible membrane is attached immediately adjacent the outlet in said base.

19. The non-invasive female urine collection device of claim 13 further including drainage means connected to said outlet for draining fluids flowing into said flow channel.

20. The non-invasive female urine collection device of claim 13 further including an outlet nipple on the outer surface of said base and in fluid communication with the outlet therein.

21. The non-invasive female urine collection device of claim 20 further including a drain conduit having a first end and connected at its first end to said outlet nipple.

22. The non-invasive female urine collection device of claim 21 further including collection means connected to a second end of said drain conduit for drawing fluids through said drain conduit and for holding said fluids.

23. The non-invasive female urine collection device of claim 13 wherein the outer surface of the flexible membrane defining the flow channel and immediately surrounding the opening of the flow channel is coated with a layer of a hydrophobic material.

24. A non-invasive female urine collection device for a female patient having legs, a perineal area and a waist, said device comprising an elongated, planar base configured to be positioned comfortably between the legs of the female patient and in contact with at least a portion of the patient's perineal area, said bas having an outlet extending between an inner surface and an outer surface thereof, said device further including a flexible membrane positioned above the inner surface of the base and having an outer circumferential edge attached to said base, said flexible membrane having an inner circumferential edge thereof which defines an open area therein, with said inner circumferential edge of said flexible membrane surrounding said outlet and attached to said inner surface of said base, with said inner circumferential edge and outer circumferential edge of said flexible membrane spaced apart from each other such that a chamber is formed between the flexible membrane and the base, with said chamber configured to be inflated and form a cushion when said flexible membrane is positioned against the patient's perineal area, with a portion of said flexible membrane adjacent said inner circumferential edge forming a flow channel which extends from an opening at an outer surface of said flexible membrane to said outlet, and with said opening of said flow channel at said flexible membrane outer surface configured to surround a patient's urethra, said device further including inflation means for inflating the chamber.

* * * * *

UNITED STATES PATENT AND TRADEMARK OFFICE
CERTIFICATE OF CORRECTION

PATENT NO. : 5,267,988
DATED : December 7, 1993
INVENTOR(S) : Barry L. Farkas

It is certified that error appears in the above-indentified patent and that said Letters Patent is hereby corrected as shown below:

Abstract Line 16 after "other" insert --such--.

Abstract Lines 25-26 "adapted configured" should read --configured--.

Claim 16 Line 2 Column 8 after "includes" delete "a".

Claim 24 Line 42 Column 8 "bas" should read --base--.

Signed and Sealed this

Twenty-fourth Day of May, 1994

Attest:

BRUCE LEHMAN

Attesting Officer    Commissioner of Patents and Trademarks